(12) United States Patent
Lee et al.

(10) Patent No.: US 9,238,138 B2
(45) Date of Patent: *Jan. 19, 2016

(54) USE OF STIMULATION PULSE SHAPE TO CONTROL NEURAL RECRUITMENT ORDER AND CLINICAL EFFECT

(75) Inventors: Dongchul Lee, Valencia, CA (US); Michael Moffitt, Valencia, CA (US); Christopher Ewan Gillespie, Stevenson Ranch, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 700 days.

This patent is subject to a terminal disclaimer.

(21) Appl. No.: 13/231,493

(22) Filed: Sep. 13, 2011

(65) Prior Publication Data

US 2012/0004707 A1    Jan. 5, 2012

Related U.S. Application Data

(63) Continuation of application No. 12/175,758, filed on Jul. 18, 2008, now Pat. No. 8,036,754.

(60) Provisional application No. 60/951,177, filed on Jul. 20, 2007.

(51) Int. Cl.
*A61N 1/36* (2006.01)
*A61N 1/372* (2006.01)
(Continued)

(52) U.S. Cl.
CPC .......... *A61N 1/3605* (2013.01); *A61N 1/36017* (2013.01); *A61N 1/36003* (2013.01); *A61N 1/36007* (2013.01); *A61N 1/36032* (2013.01); *A61N 1/36046* (2013.01);
(Continued)

(58) Field of Classification Search
None
See application file for complete search history.

(56) References Cited

U.S. PATENT DOCUMENTS 4,612,934 A    9/1986    Borkan
4,821,724 A    4/1989    Whigham et al.
(Continued)

FOREIGN PATENT DOCUMENTS

EP    0781153 B1    2/2003
EP    0 781 153    12/2003
(Continued)

OTHER PUBLICATIONS

PCT International Search Report dated Oct. 29, 2008 for Application No. PCT/US2008/070429, Applicant: Boston Scientific Neuromodulation Corporation, Form PCT/ISA/220 and PCT/ISA/210 (8 pages).

(Continued)

*Primary Examiner* — Kennedy Schaetzle
(74) *Attorney, Agent, or Firm* — Schwegman Lundberg & Woessner, P.A.

(57) ABSTRACT

A method, electrical tissue stimulation system, and programmer for providing therapy to a patient are provided. Electrodes are placed adjacent tissue (e.g., spinal cord tissue) of the patient, electrical stimulation energy is delivered from the electrodes to the tissue in accordance with a defined waveform, and a pulse shape of the defined waveform is modified, thereby changing the characteristics of the electrical stimulation energy delivered from the electrode(s) to the tissue. The pulse shape may be modified by selecting one of a plurality of different pulse shape types or by adjusting a time constant of the pulse shape.

29 Claims, 15 Drawing Sheets

(51) Int. Cl.
*A61N 1/378* (2006.01)
*A61N 1/39* (2006.01)

(52) U.S. Cl.
CPC ............ *A61N 1/36146* (2013.01); *A61N 1/378* (2013.01); *A61N 1/37247* (2013.01); *A61N 1/3906* (2013.01)

(56) References Cited

U.S. PATENT DOCUMENTS

| | | | |
|---|---|---|---|
| 5,184,616 | A | 2/1993 | Weiss |
| 5,725,560 | A | 3/1998 | Brink |
| 6,393,325 | B1 | 5/2002 | Mann et al. |
| 6,516,227 | B1 | 2/2003 | Meadows et al. |
| 6,560,490 | B2 | 5/2003 | Grill et al. |
| 6,671,556 | B2 | 12/2003 | Osorio et al. |
| 6,845,271 | B2 | 1/2005 | Fang et al. |
| 6,850,802 | B2 | 2/2005 | Holsheimer |
| 6,895,280 | B2 | 5/2005 | Meadows et al. |
| 6,909,917 | B2 | 6/2005 | Woods et al. |
| 6,934,580 | B1 | 8/2005 | Osorio et al. |
| 6,993,384 | B2 | 1/2006 | Bradley et al. |
| 7,149,579 | B1 * | 12/2006 | Koh et al. ............... 607/19 |
| 7,317,948 | B1 | 1/2008 | King et al. |
| 8,036,754 | B2 * | 10/2011 | Lee et al. ............... 607/72 |
| 2002/0019650 | A1 | 2/2002 | Craggs et al. |
| 2002/0052632 | A1 | 5/2002 | Ben-Haim et al. |
| 2002/0055779 | A1 | 5/2002 | Andrews |
| 2002/0143365 | A1 | 10/2002 | Herbst |
| 2003/0139781 | A1 | 7/2003 | Bradley et al. |
| 2004/0186521 | A1 | 9/2004 | Rubin et al. |
| 2004/0210271 | A1 | 10/2004 | Campen et al. |
| 2005/0267546 | A1 | 12/2005 | Parramon et al. |
| 2006/0069415 | A1 | 3/2006 | Cameron et al. |
| 2006/0149337 | A1 | 7/2006 | John |
| 2006/0173493 | A1 | 8/2006 | Armstrong et al. |
| 2006/0173494 | A1 | 8/2006 | Armstrong et al. |
| 2006/0265027 | A1 * | 11/2006 | Vaingast et al. ............... 607/62 |
| 2007/0038250 | A1 | 2/2007 | He et al. |
| 2007/0043401 | A1 | 2/2007 | John |
| 2007/0066971 | A1 | 3/2007 | Podhajsky |
| 2007/0097593 | A1 | 5/2007 | Armstrong |
| 2007/0129720 | A1 | 6/2007 | Demarais et al. |
| 2007/0225765 | A1 | 9/2007 | King |
| 2007/0299482 | A1 | 12/2007 | Littlewood et al. |
| 2008/0065167 | A1 | 3/2008 | Boggs, II et al. |
| 2008/0071321 | A1 | 3/2008 | Boggs, II et al. |

FOREIGN PATENT DOCUMENTS

| | | |
|---|---|---|
| EP | 2190527 B1 | 7/2013 |
| JP | 2005511164 | 4/2005 |
| JP | 2013163112 A | 8/2013 |
| WO | WO 87/07511 | 12/1987 |
| WO | WO 96/09852 | 4/1996 |
| WO | WO 97/15351 | 5/1997 |
| WO | WO 03/047685 | 6/2003 |
| WO | WO 2007/048087 | 4/2007 |
| WO | WO-2007048087 A3 | 4/2007 |
| WO | WO 2008/017055 | 2/2008 |
| WO | WO-2008017055 A3 | 2/2008 |
| WO | WO-2009015005 | 1/2009 |

OTHER PUBLICATIONS

PCT Written Opinion dated Oct. 29, 2008 for Application No. PCT/US2008/070429, Applicant: Boston Scientific Neuromodulation Corporation, Form PCT/ISA/237 (8 pages).

PCT International Preliminary Report on Patentability (Chapter I of the Patent Cooperation Treaty) for Application No. PCT/US2008/070429, Applicant: Boston Scientific Neuromodulation Corporation, Form PCT/IB/326 and 373, dated Jan. 26, 2010 (8pages).

EPO Communication dated Dec. 21, 2010 in related EP Application No. 08 782 036.1-2305, Applicant: Boston Scientific Neuromodulation Corporation, (4pages).

Canadian Office Communication dated Jan. 21, 2013 in Canadian Patent Application No. 2694498, Applicant: Boston Scientific Neuromodulation Corporation (3pages).

Canadian Office Communication dated Dec. 10, 2013 in Canadian Patent Application No. 2694498, Applicant: Boston Scientific Neuromodulation Corporation (3pages).

Japanese Office Communication dated Jan. 29, 2013 in Japanese Patent Application No. 2010-518306, Applicant: Boston Scientific Neuromodulation Corporation (3pages) including English Translations prepared by Nakamura & Partners (3pages).

Japanese Office Communication dated Mar. 25, 2014 in Japanese Patent Application No. 2013-114262, Applicant: Boston Scientific Neuromodulation Corporation, English Translations prepared by Nakamura & Partners (2pages).

EPO Office Communication dated Dec. 15, 2011 in European Patent Application No. 08782036.1-2305, Applicant: Boston Scientific Neuromodulation Corporation (4pages).

EPO Office Communication dated Apr. 4, 2013 in European Patent Application No. 12199556.7-1652, Applicant: Boston Scientific Neuromodulation Corporation (4pages).

EPO Office Communication dated Feb. 11, 2014 in European Patent Application No. 12199556.7-1652, Applicant: Boston Scientific Neuromodulation Corporation (3pages).

EPO Office Communication dated Dec. 5, 2013 in European Patent Application No. 12199558.3-1652, Applicant: Boston Scientific Neuromodulation Corporation (3pages).

EPO Office Communication dated Apr. 4, 2013 in European Patent Application No. 12199558.3-1652, Applicant: Boston Scientific Neuromodulation Corporation (5pages).

"U.S. Appl. No. 12/175,758, Non Final Office Action mailed Mar. 3, 2011", 11 pgs.

"U.S. Appl. No. 12/175,758, Notice of Allowance mailed Jun. 10, 2011", 7 pgs.

"U.S. Appl. No. 12/175,758, Response filed Apr. 12, 2011 to Non Final Office Action mailed Mar. 3, 2011", 8 pgs.

"European Application Serial No. 08782036.1, Decision to Grant mailed Jun. 6, 2013", 2 pgs.

"European Application Serial No. 08782036.1, Examination Notification Art. 94(3) mailed Dec. 15, 2011", 4 pgs.

"European Application Serial No. 08782036.1, Response filed Apr. 24, 2012 to Examination Notification Art. 94(3) mailed Dec. 15, 2011", 9 pgs.

"European Application Serial No. 08782036.1, Response filed Apr. 28, 2011 to Examination Notification Art. 94(3) mailed Dec. 21, 2010", 10 pgs.

"European Application Serial No. 08782036.1, Summons to Attend Oral Proceeding mailed May 18, 2012", 5 pgs.

"European Application Serial No. 12199556.7, Examination Notification Art. 94(3) mailed Feb. 11, 2014", 3 pgs.

"European Application Serial No. 12199556.7, Extended European Search Report mailed Apr. 4, 2013", 5 pgs.

"European Application Serial No. 12199556.7, Office Action mailed May 6, 2013", 2 pgs.

"European Application Serial No. 12199556.7, Response filed Apr. 28, 2014 to Examination Notification Art. 94(3) mailed Feb. 11, 2014", 7 pgs.

"European Application Serial No. 12199556.7, Response filed Nov. 4, 2013 to Office Action mailed May 6, 2013", 2 pgs.

"European Application Serial No. 12199556.7, Summons to Attend Oral Proceeding mailed Jan. 21, 2015", 1 pg.

"European Application Serial No. 12199556.7, Summons to Attend Oral Proceeding mailed Feb. 4, 2015", 5 pgs.

"European Application Serial No. 12199556.7, Summons to Attend Oral Proceedings mailed Mar. 30, 2015", 1 pg.

"European Application Serial No. 12199558.3, Examination Notification Art. 94(3) mailed Dec. 5, 2013", 3 pgs.

"European Application Serial No. 12199558.3, Extended European Search Report mailed Apr. 4, 2013", 5 pgs.

"European Application Serial No. 12199558.3, Office Action mailed May 6, 2013", 2 pgs.

"European Application Serial No. 12199558.3, Response filed Apr. 4, 2014 to Examination Notification Art. 94(3) mailed Dec. 5, 2013", 3 pgs.

(56) References Cited

OTHER PUBLICATIONS

"European Application Serial No. 12199558.3, Response filed Nov. 4, 2013 to Office Action mailed May 6, 2013", 2 pgs.

"European Application Serial No. 12199558.3, Summons to Attend Oral Proceeding mailed Jan. 19, 2015", 5 pgs.

"European Application Serial No. 12199558.3, Summons to Attend Oral Proceedings mailed Mar. 30, 2015", 1 pg.

"International Application Serial No. PCT/US2008/070429, International Preliminary Report on Patentability mailed Oct. 13, 2008", 10 pgs.

"International Application Serial No. PCT/US2008/070429, International Search Report mailed Oct. 29, 2008", 4 pgs.

"International Application Serial No. PCT/US2008/070429, Written Opinion mailed Oct. 29, 2008", 8 pgs.

"Japanese Application Serial No. 2013-114262, Office Action mailed Jan. 19, 2015", With English Translation, 5 pgs.

"Japanese Application Serial No. 2013-114262, Office Action mailed Apr. 3, 2014", English Translation only, 2.

"Japanese Application Serial No. 2013-114262, Response filed Jul. 1, 2014 to Office Action mailed Mar. 25, 2014", English Claims, 3 pgs.

\* cited by examiner

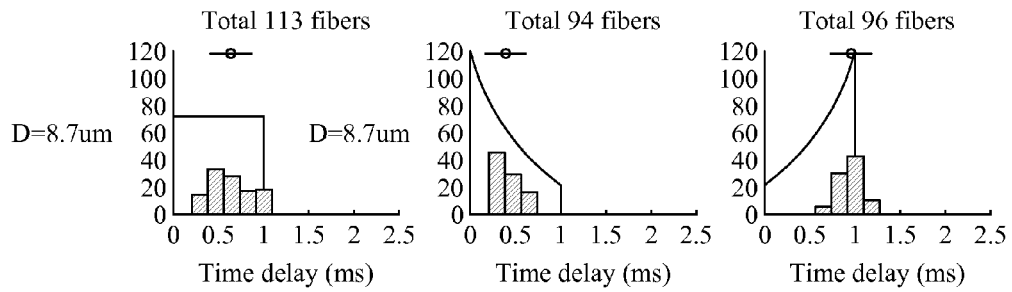
FIG. 4A  FIG. 4B  FIG. 4C
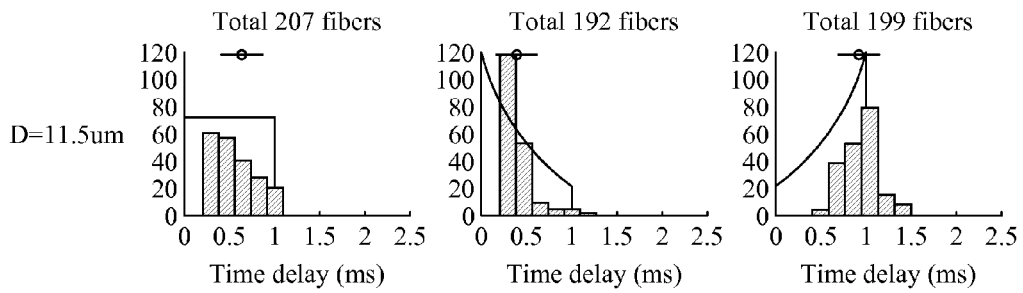
FIG. 5A  FIG. 5B  FIG. 5C
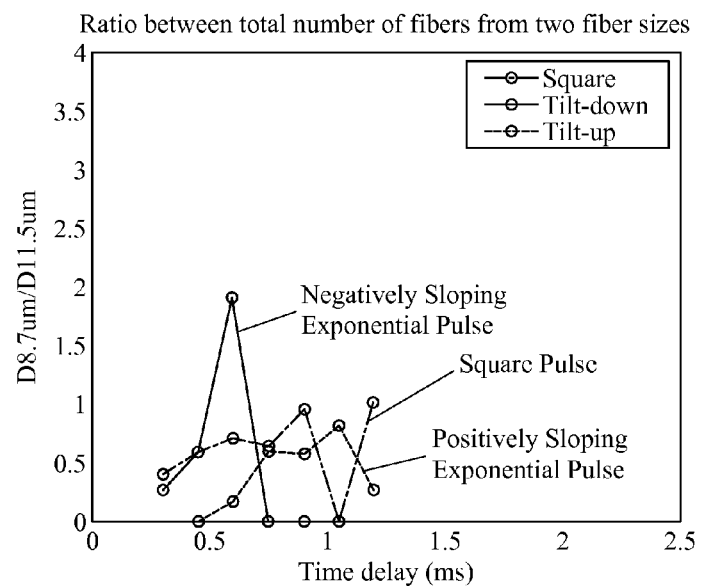
FIG. 6

USE OF STIMULATION PULSE SHAPE TO CONTROL NEURAL RECRUITMENT ORDER AND CLINICAL EFFECT

RELATED APPLICATION

The present application is a continuation of U.S. patent application Ser. No. 12/175,758, filed Jul. 18, 2008, which claims the benefit under 35 U.S.C. §119 to U.S. Provisional Patent Application Ser. No. 60/951,177, filed Jul. 20, 2007. The foregoing applications hereby expressly incorporated by reference into the present application in their entireties.

FIELD OF THE INVENTION

The present inventions relate to tissue stimulation systems, and more particularly, to systems and methods for adjusting the stimulation provided to tissue to optimize a therapeutic effect.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, and rate of the stimulation pulses. The shape of the electrical pulses delivered by present neurostimulation systems are ideally square, but are often shaped by both passive circuit components, as well as physiological tissues, which typically have non-linear electrical properties. The neurostimulation system may further comprise a handheld patient programmer to remotely instruct the neurostimulator to generate electrical stimulation pulses in accordance with selected stimulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Typically, the therapeutic effect for any given neurostimulation application may be optimized by adjusting the stimulation parameters. Often, these therapeutic effects are correlated to the diameter of the nerve fibers that innervate the volume of tissue to be stimulated. For example, in SCS, activation (i.e., recruitment) of large diameter sensory fibers is believed to reduce/block transmission of smaller diameter pain fibers via interneuronal interaction in the dorsal horn of the spinal cord. Activation of large sensory fibers also creates a sensation known as paresthesia that can be characterized as an alternative sensation that replaces the pain signals sensed by the patient. Thus, it has been believed that the large diameter nerve fibers are the major targets for SCS. However, over-stimulation of the large diameter nerve fibers may lead to other uncomfortable, intense sensations in unwanted areas, thereby producing a side effect, and in the case of SCS, limit therapeutic coverage. Therefore, control of nerve fiber recruitment based on size might be critically important to maximize the therapeutic effect of SCS. It is also believed that controlling the order in which differently sized nerve fibers are recruited, as well as the temporal synchronization (simultaneously recruiting nerve fibers with a single pulse) and desynchronization (recruiting nerve fibers at different times with a single pulse), may further maximize the therapeutic effect of SCS.

Thus, a neurostimulation system that could selectively activate different fiber diameters in a controllable manner would be valuable to "tune" the desired therapeutic effect of a neurostimulation application, such as SCS. It would also be valuable to provide additional stimulation parameters that can be adjusted to further optimize the therapeutic effect of the stimulation irrespective of the ability to recruit differently sized nerve fibers in a controlled manner.

SUMMARY OF THE INVENTION

In accordance with a first aspect of the present inventions, a method of providing therapy to a patient is provided. The method comprises placing one or more electrodes adjacent to tissue (e.g., spinal cord tissue) of the patient, delivering electrical stimulation energy from the electrode(s) to the tissue in accordance with a defined waveform, and modifying a pulse shape of the defined waveform, thereby changing the characteristics of the electrical stimulation energy delivered from the electrode(s) to the tissue.

In one method, the pulse shape is modified by selecting one of a plurality of different pulse shape types (e.g., a square pulse, an exponential pulse, a logarithmic pulse, a ramped pulse, a trapezoidal pulse, or a combination thereof). The different pulse types may, e.g., comprise a negatively sloping pulse, such as a negatively sloping exponential pulse or a negatively sloping linear ramp pulse, and a positively sloping pulse, such as a positively sloping exponential pulse or a positively sloping linear ramp pulse. In another method, the pulse shape is modified by adjusting a time constant of the pulse shape.

The pulse shape and other pulse parameters (e.g., pulse amplitude, pulse duration, and pulse rate) of the defined waveform may be modified independent of each other or dependent upon each other. In the latter case, at least one of the other pulse parameters may be modified in response to the modification of the pulse shape to advantageously maintain a substantially uniform charge of the electrical stimulation energy. An optional method comprises measuring one or more electrical characteristics of the tissue (e.g., impedance), wherein the pulse shape is modified based on the measured electrical characteristics. As one example, the pulse shape may be modified in response to a change in the measured electrical characteristics.

In accordance with a second aspect of the present inventions, a neurostimulation system is provided. The neurostimulation system comprises one or more electrical terminals configured for being coupled to one or more stimulation leads, output stimulation circuitry capable of outputting electrical stimulation energy to the electrical terminal(s) in accordance with a defined waveform, and control circuitry configured for modifying a pulse shape of the defined waveform, thereby changing the characteristics of the electrical stimulation energy outputted to the electrical terminal(s). In one embodiment, the control circuitry is configured for modifying the pulse shape by selecting one of a plurality of different pulse shape types; for example, any of the different pulse shape types set forth above. In another embodiment, the control circuitry is configured for modifying the pulse shape by adjusting a time constant of the pulse shape.

The control circuitry may be configured for modifying the pulse shape and other pulse parameters of the defined waveform independent of each other or dependent upon each other. In the latter case, the control circuitry may be configured for modifying at least one of the other parameters in response to the modification of the pulse shape to maintain a substantially uniform charge of the electrical stimulation energy. In an optional embodiment, the neurostimulation system further comprises monitoring circuitry configured for measuring one or more electrical characteristics (e.g., an impedance) of the tissue, wherein the control circuitry is configured for modifying the pulse shape based on the measured electrical characteristics. For example, the control circuitry may be configured for modifying the pulse shape in response to a change in the measured one or more electrical characteristics.

The pulse shape of the defined waveform may be modified in any one or more of a variety of manners. For example, the output stimulation circuitry may comprise a plurality of different analog shaping circuits, in which case, the control circuitry may be configured for modifying the pulse shape by selecting one of the different analog shaping circuits. The control circuitry may also be configured for modifying the pulse shape by adjusting a characteristic of at least one analog electrical component in the output stimulation circuitry. In one embodiment, the pulsed waveform is formed of a stepwise function of amplitude levels or sub-pulse durations, in which case, the control circuitry may be configured for modifying the pulse shape by adjusting the amplitude levels or sub-pulse durations.

In one embodiment, the neurostimulation system further comprises a stimulation lead carrying at least one electrode electrically coupled to the electrical terminal(s). In another embodiment, the neurostimulation system further comprises memory capable of storing a parameter defining the pulse shape. In still another embodiment, the neurostimulation system further comprises telemetry circuitry capable of wirelessly receiving instructions from an external programmer to modify the pulse shape. In yet another embodiment, the neurostimulation further comprises a case containing the electrical terminal(s), output stimulation circuitry, and control circuitry to form a neurostimulator (e.g., an implantable neurostimulator).

In accordance with a third aspect of the present inventions, a programmer for a neurostimulator is provided. The programmer comprises a user interface capable of receiving an input from a user, a processor configured for generating a plurality of stimulation parameter sets defining a plurality of different pulse shapes in response to the user input, and output circuitry configured for transmitting the plurality of stimulation parameter sets to the neurostimulator. In one embodiment, the plurality of different pulse shapes comprises a plurality of different pulse shape types; for example, any of the different pulse shape types set forth above. In another embodiment, the plurality of different pulse shapes comprises a plurality of pulse shapes of the same type (e.g., exponentially decaying pulse amplitude) but with different time constants.

The processor may be configured for defining the pulse shape and other pulse parameters in each stimulation parameter set independent of each other or dependent upon each other. In the latter case, the processor may be configured for defining at least one of the other pulse parameter in response to the definition of the pulse shape to maintain a substantially uniform charge between the respective stimulation parameter sets. In one embodiment, the plurality of different pulse shapes is defined based on one or more measured electrical characteristics (e.g., an impedance) of tissue; for example by defining the pulse shapes in response to a change in the measured electrical characteristics. In another embodiment, the programmer may comprise a user interface that includes an actuator, in which case, the processor may be configured for generating the plurality of stimulation parameter sets (e.g., the different pulse shapes) in response to actuation of the actuator. In still another embodiment, the output circuitry is telemetry circuitry capable of wirelessly transmitting the plurality of stimulation parameter sets to the neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 4A-4C are histograms of the number of 8.7 μm diameter nerve fibers that are recruited over a time in response to a square pulse, a negatively sloping exponential pulse, and a positively sloping exponential pulse;

FIGS. 5A-5C are histograms of the number of 11.5 μm diameter nerve fibers that are recruited over a time in response to a square pulse, a negatively sloping exponential pulse, and a positively sloping exponential pulse;

FIG. 6 is a diagram of recruitment ratio of the total number of 8.7 μm diameter nerve fibers versus 11.5 μm diameter nerve fibers over time in response to the application of the square pulse, negatively sloping exponential pulse, and positively sloping exponential pulse;

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
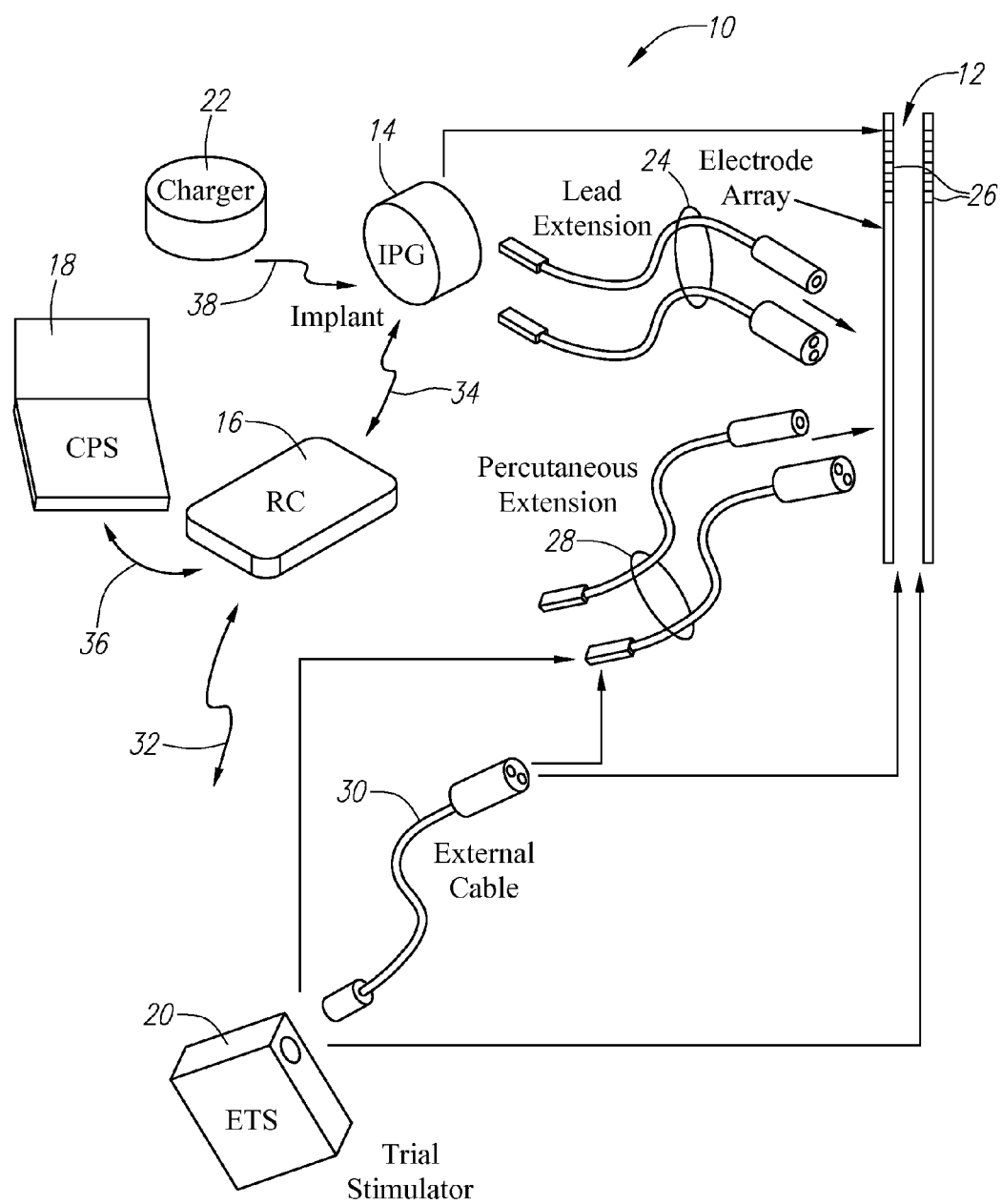
FIG. 1 is plan view of one embodiment of a spinal cord stimulation (SCS) system arranged in accordance with the present inventions.

Turning first to FIG. 1, an exemplary SCS system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers the electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
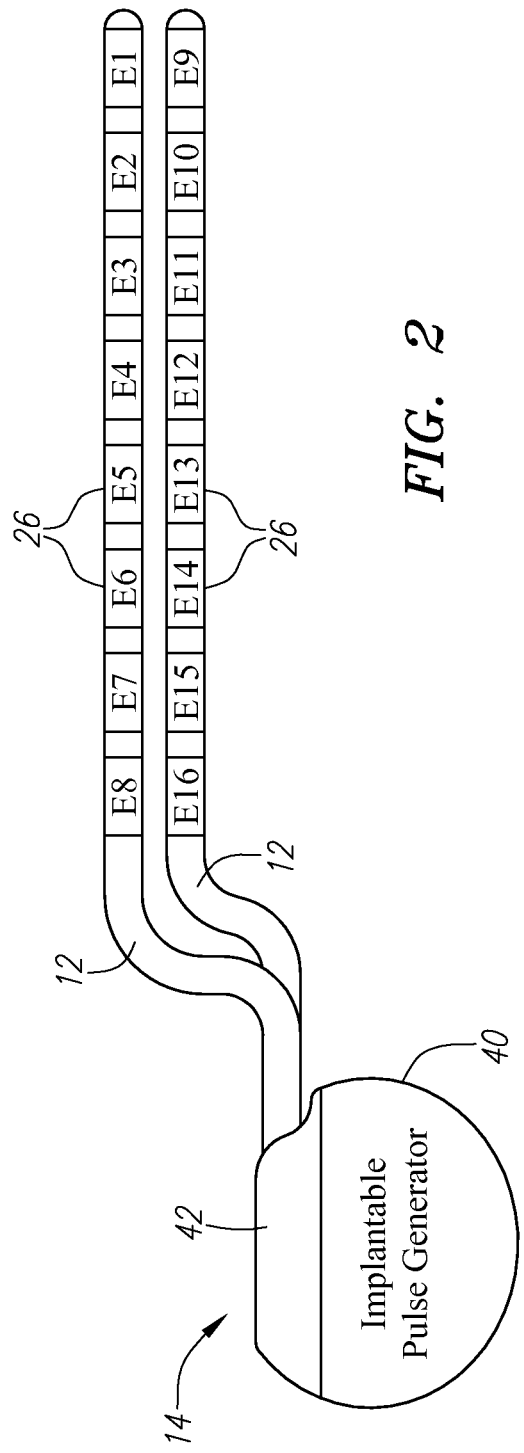
FIG. 2 is a profile view of an implantable pulse generator (IPG) used in the SCS system of FIG. 1.

Referring now to FIG. 2, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes pulse generation circuitry that delivers the electrical stimulation energy in the form of a pulsed electrical waveform to the electrode array 26 in accordance with a set of stimulation parameters. Such stimulation parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrode array 26), pulse duration (measured in microseconds), and pulse rate (measured in pulses per second), and as will be described in further detail below, a pulse shape.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

Figure 3A:
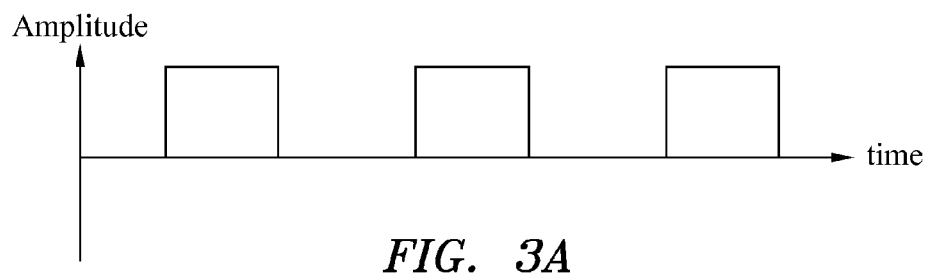
FIGS. 3A-3L are diagrams of various stimulation pulse shapes that can be generated by the system of FIG. 1.
Figure 3B:
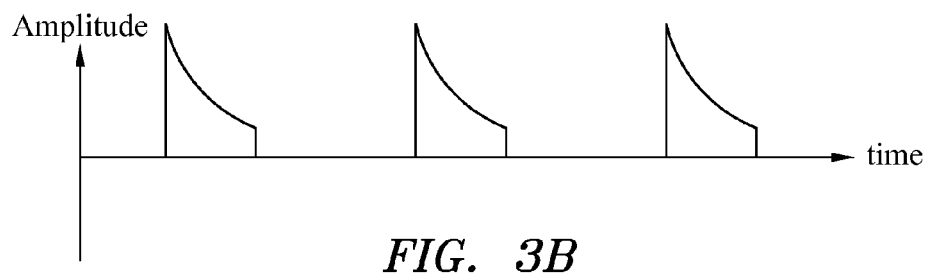
Figure 3C:
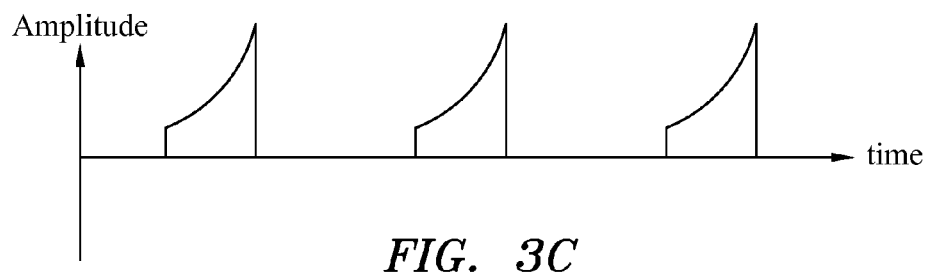
Figure 3D:
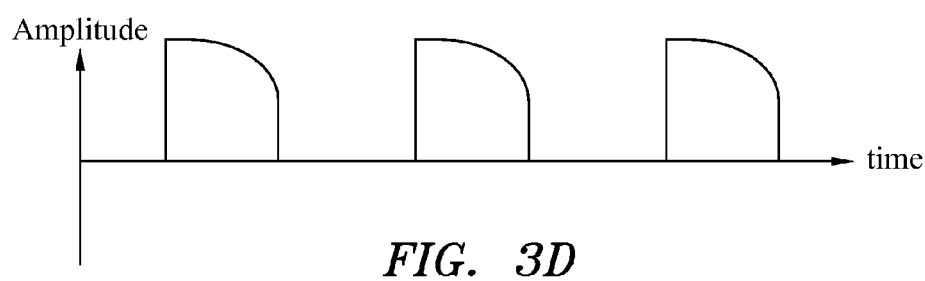
Figure 3E:
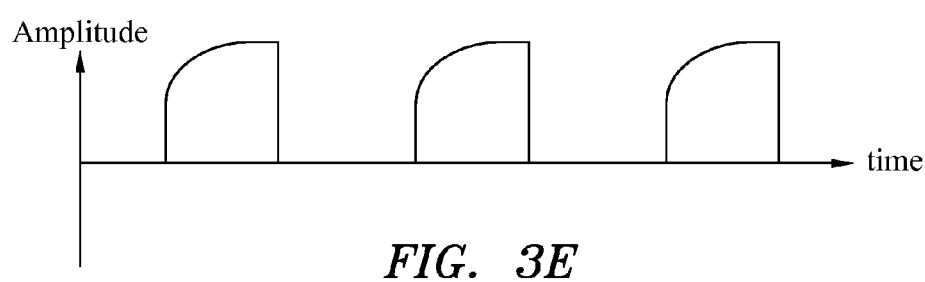
Figure 3F:
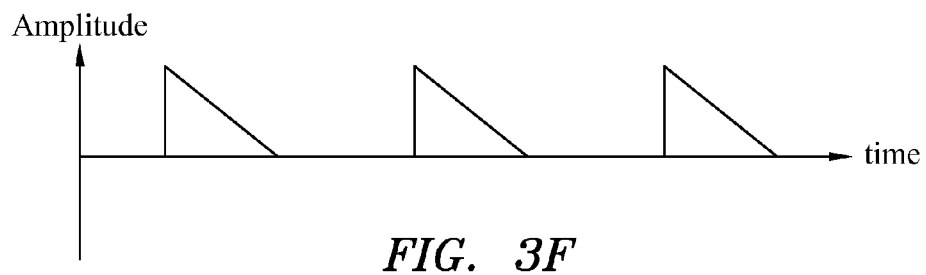
Figure 3G:
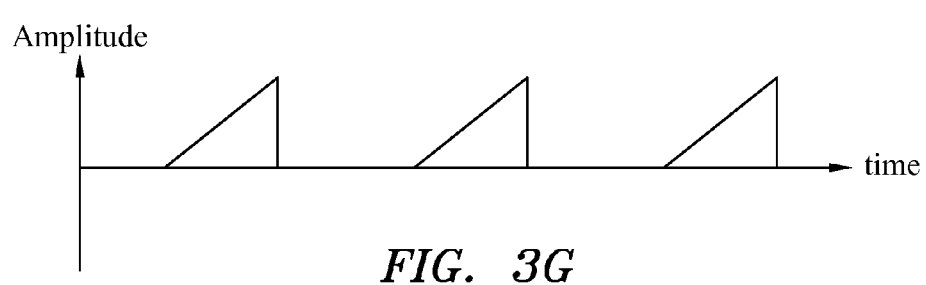
Figure 3H:
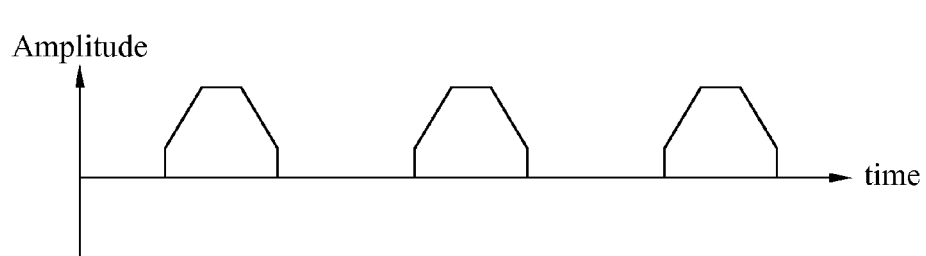
Figure 3I:
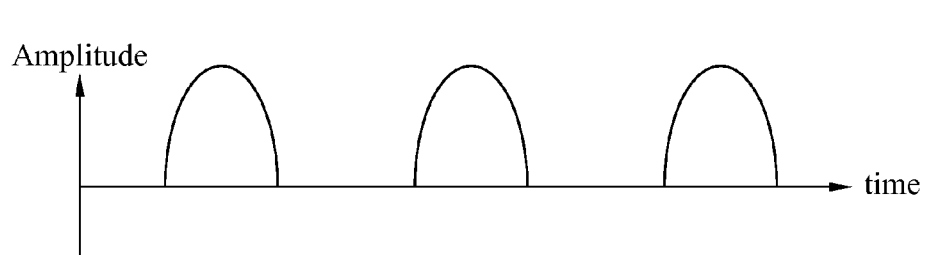
Figure 3J:
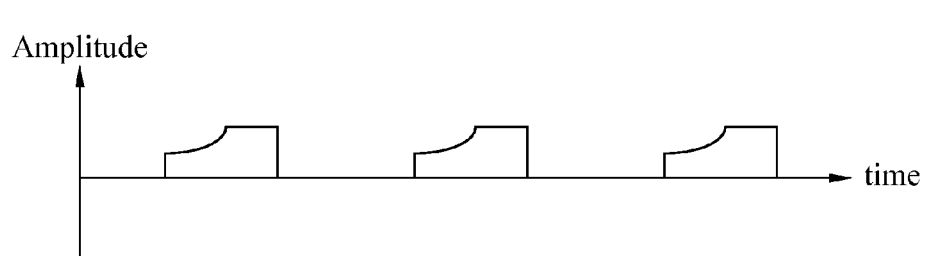
Figure 3K:
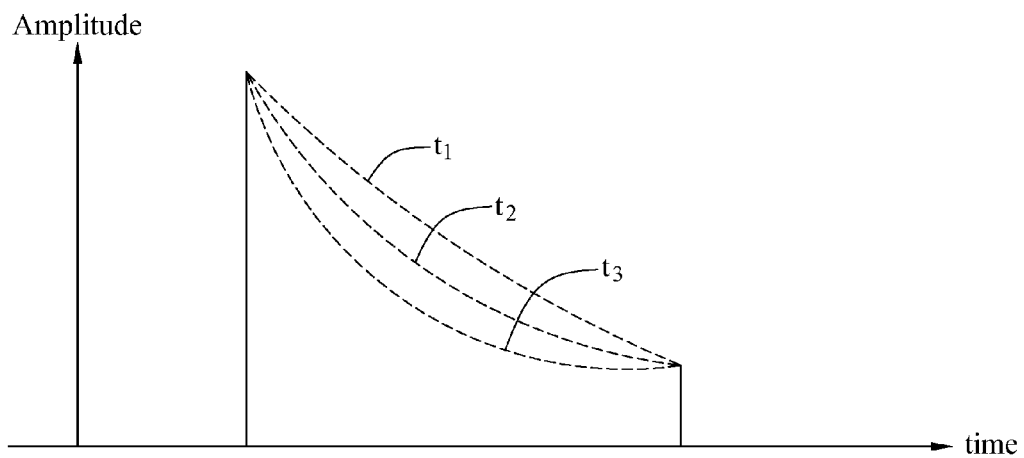
Figure 3L:
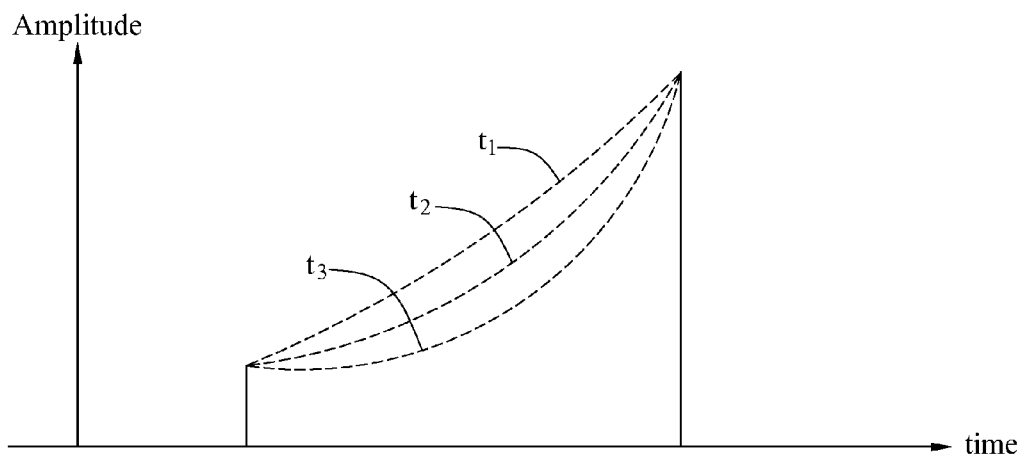

Significant to the present inventions, the stimulation parameters, and in particular the electrical pulse parameters, further comprise a pulse shape (as opposed to a pulse size that would include pulse amplitude and pulse width or duration). The pulse shape may be defined by a pulse shape type. FIGS. 3A-3I illustrate different exemplary pulse shape types that can be generated by the IPG 14. For example, the pulsed waveform may be a square pulse (FIG. 3A), a negatively sloping exponential pulse (FIG. 3B), a positively sloping exponential pulse (FIG. 3C), a negatively sloping logarithmic pulse (FIG. 3D), a positively sloping logarithmic pulse (FIG. 3E), a negatively sloping ramped pulse (FIG. 3F), a positively sloping ramped pulse (FIG. 3G), a trapezoidal waveform (FIG. 3H), a sinusoidal waveform (FIG. 3I), or a combination of any of the foregoing; for example, a positively sloping exponential/square pulse (FIG. 3J). The pulse shape may also be defined by a slope characteristic within the same pulse shape type. FIGS. 3K and 3L illustrates different slope changes for the same pulse shape type, and in particular different time constants t1-t3 for the negatively sloping exponential pulse (FIG. 3K), and different time constants t1-t3 for the positively sloping exponential pulse (FIG. 3L). Thus, the shape of a pulse may be changed by modifying the pulse type or modifying a slope characteristic of the pulse (that is not caused by merely changing the amplitude or duration of the pulse).

While the relationship between the pulse shape and the clinical effects on tissue is not well known, it has been discovered that different pulse shapes will effect different neural recruitment orders for different sizes of the nerve fibers and will effect different temporal synchronization of the action potential initiation (i.e., recruitment) of nerve fibers, thereby controlling the clinical effect of the electrical stimulation energy. For example, using conventional nerve fiber modeling techniques, it has been discovered that the temporal recruitment response differences between 8.7 μm diameter nerve fibers and 11.5 μm diameter nerve fibers largely depend on the shape of the applied electrical pulse.

In particular, FIGS. 4A-4C respectively illustrate histograms of the number of 8.7 μm diameter nerve fibers that are recruited over a time in response to a square pulse (FIG. 4A), a negatively sloping exponential pulse (FIG. 4B), and a positively sloping exponential pulse (FIG. 4C), and FIGS. 5A-5C respectively illustrate histograms of the number of 11.5 μm diameter nerve fibers that are recruited over time in response to the application of the same square pulse (FIG. 5A), negatively sloping exponential pulse (FIG. 5B), and positively sloping exponential pulse (FIG. 5C).

As can be extrapolated from FIGS. 4A and 5A, a square pulse recruits a relatively high number of large nerve fibers at the beginning of the pulse, which number gradually decreases with time, and substantially recruits a uniform number of small nerve fibers along the duration of the pulse. As can be extrapolated from FIGS. 4B and 5B, a negatively sloping exponential pulse recruits a relative high number of both large and small nerve fibers at the beginning of the pulse, which numbers gradually decrease with time. As can be extrapolated from FIGS. 4C and 5C, a positively sloping exponential pulse recruits a relative low number of both large and small nerve fibers at the beginning of the pulse, which numbers gradually increase with time.

FIG. 6 illustrates the recruitment ratio of the total number of 8.7 μm diameter nerve fibers versus 11.5 μm diameter nerve fibers over time in response to the application of the square pulse, negatively sloping exponential pulse, and positively sloping exponential pulse. Based on a straight line fitting of the data in FIG. 6, the recruitment ratio is relatively uniform over time in response to a square pulse, the recruitment ratio increases over time in response to a negatively sloping exponential pulse, and the recruitment ratio decreases over time in response to a positively sloping exponential pulse. Thus, it is clear from the foregoing that the time ordered recruitment of large and small nerve fibers depends on the pulse shape, thereby providing another means of optimizing the stimulation energy output by the IPG 14 in addition to modifying the pulse amplitude, pulse rate, and pulse duration.

Figure 7:
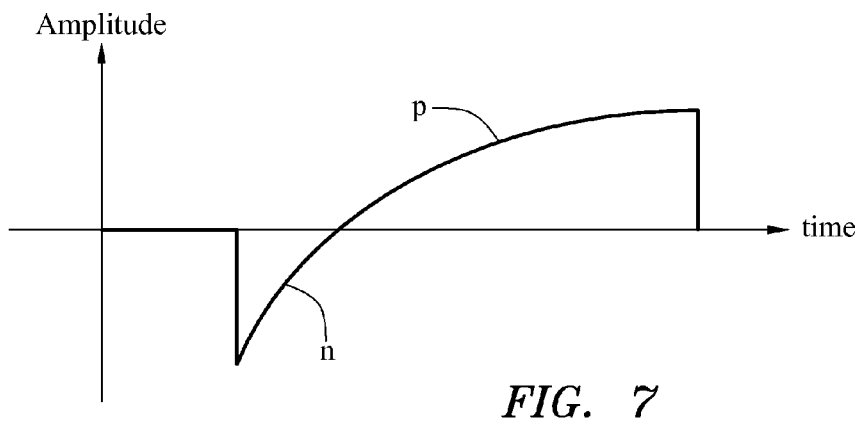
FIG. 7 is a diagram of a stimulation pulse that can be generated by the system of FIG. 1, wherein the stimulation pulse is particularly shown having a negatively polarized portion and a positively polarized portion.
Figure 8:
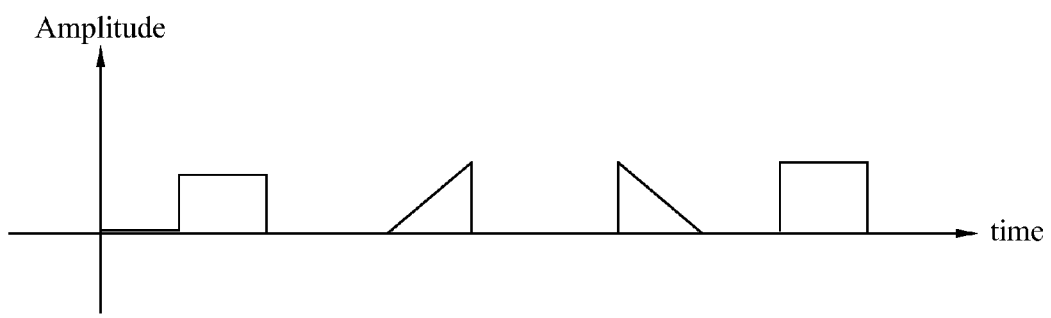
FIG. 8 is a diagram of a pulse train of different pulse shape types that can be generated by the system of FIG. 1.

While the pulse shape types described above have been shown as having a single polarity (in this case, positive), it should be noted that a pulse shape type can have more than one polarity. For example, FIG. 7 illustrates a pulse, and in particular, a positively sloping logarithmic pulse that has a negatively polarized portion n followed by a positively polarized portion p. It is believed that pulses that transition from one polarity to the next may enable improved discrimination between fiber types. Also, while the series of the pulses (i.e., the pulse trains) described above have been shown as having a uniform pulse type, a single pulse train may have a variety of pulse types. For example, FIG. 8 illustrates a pulse train having a square pulse, followed by a positively sloping ramp pulse, followed by a negatively sloping ramp pulse. In the context of SCS, it is believed that the use of a train of multiple pulse types with a single electrode combination may be able to broaden paresthesia coverage by exciting different nerve populations.

Figure 9:
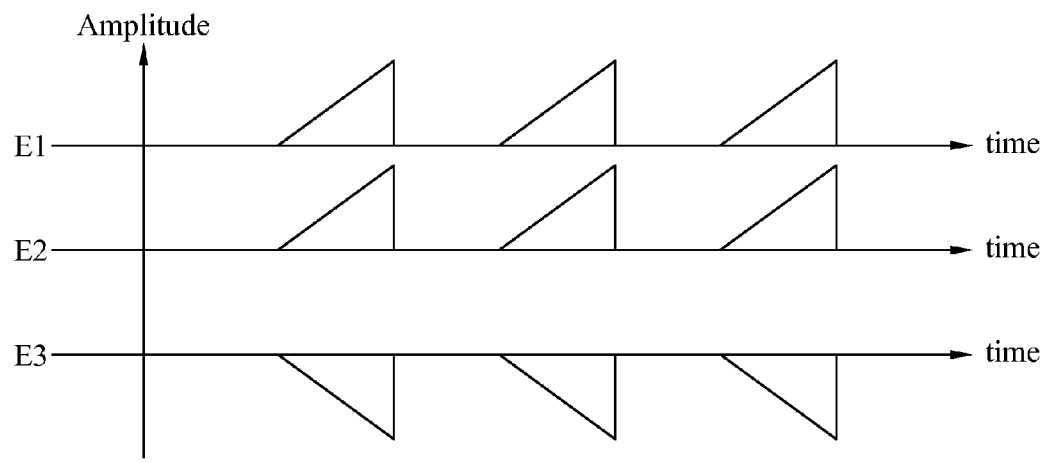
FIG. 9 is a diagram of a stimulation pulse that can be generated for a single group of electrodes by the system of FIG. 1.
Figure 10:
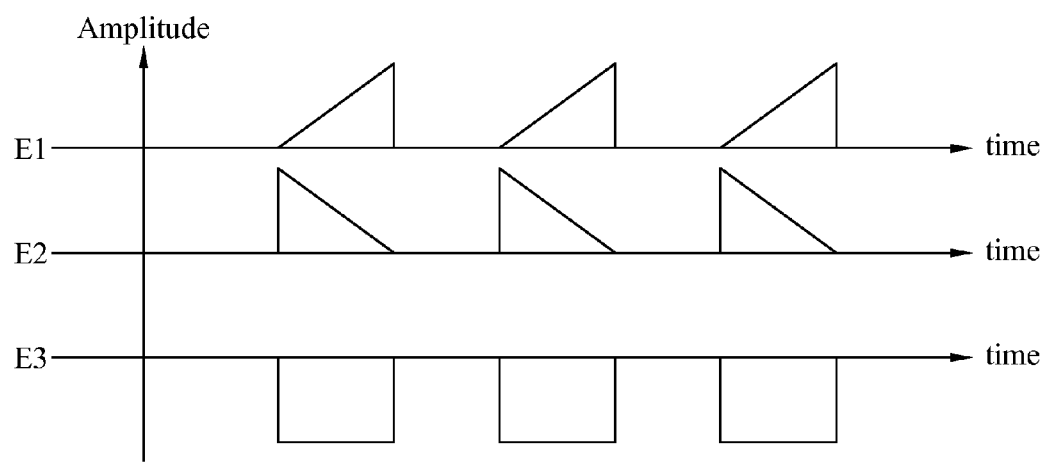
FIG. 10 is a diagram of different stimulation pulses that can be independently generated for electrodes by the system of FIG. 1.

It should be appreciated that a single pulse type can be generated for the electrodes of a group. For example, given an electrode combination E1-E3, with electrode E1 and E2 as anodic electrodes, and electrode E3 as a cathodic electrode, a single positively sloping anodic ramp pulse can be generated on electrodes E1 and E2 as a group, as shown in FIG. 9. Because the net sum of the electrical current flowing through electrodes E1-E3 must be zero (based on the preservation of current), a larger negatively sloping cathodic ramp pulse (equal to the sum of the current generated at electrodes E1 and E2) is generated at electrode E3. It should also be appreciated that different pulse shape types can be independently generated for the electrodes in a single group. For example, a positively sloping anodic ramp pulse can be generated on electrode E1, and a negatively sloping anodic ramp pulse can be simultaneously generated on electrode E2, as shown in FIG. 10. Again, because the net sum of the electrical current flowing through the net sum of the electrode current flowing through electrodes E1-E3 must be zero, a cathodic square pulse is generated on electrode E3.

Figure 11:
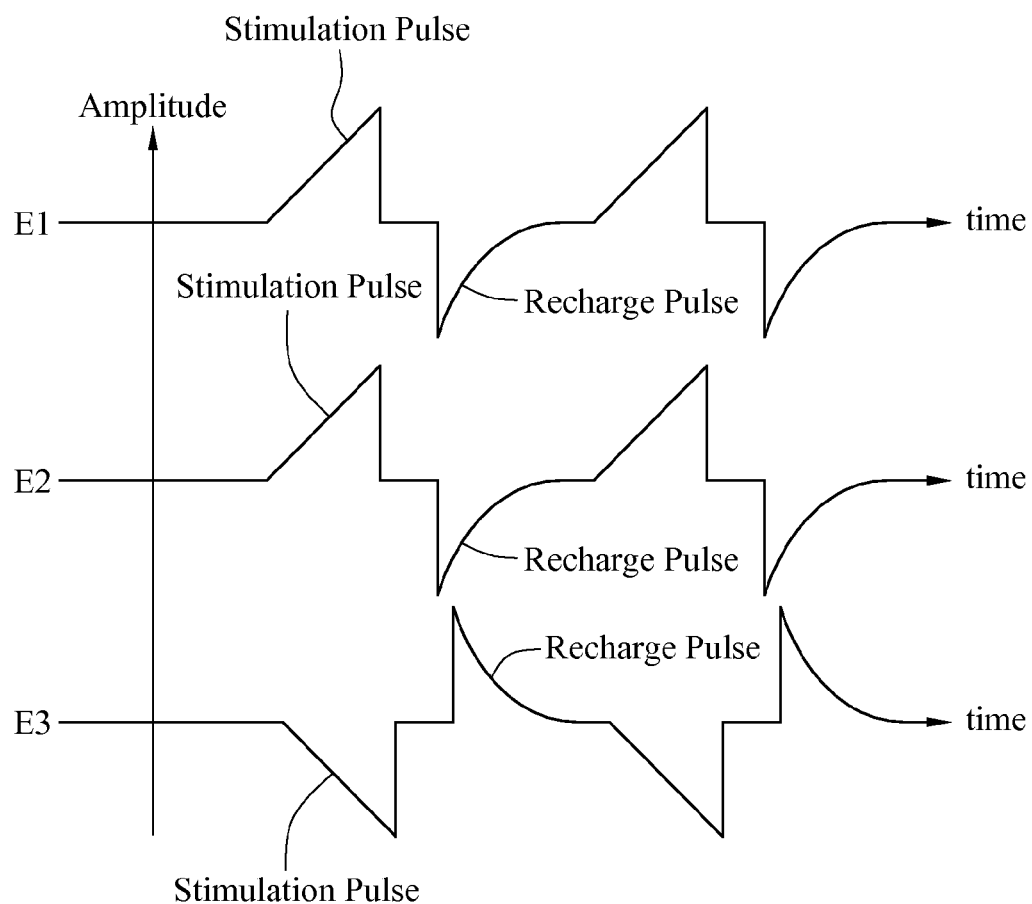
FIG. 11 is a diagram of stimulation pulses and recharge pulses that can be generated for a single group of electrodes by the system.

While the pulse shape can be modified when used as a stimulation pulse (i.e., a pulse that performs the actual stimulation), the pulse shape also be modified when used as a recharge pulse (i.e., a charge that is generated after a stimulation pulse to prevent direct current charge transfer through the tissue, thereby avoiding electrode degradation and cell trauma). That is, charge is conveyed through the electrode-tissue interface via current at an electrode during a stimulation period, and then pulled back off the electrode-tissue interface via an oppositely polarized current at the same electrode during a recharge period. For example, assuming that current is delivered to electrodes E1-E3 during a stimulation period, as shown in FIG. 9, a recharge pulse can be generated on electrodes E1-E3 as shown in FIG. 11. The shape of the recharge pulses can be modified in the same manner as the stimulation pulses. In the SCS context, it is believed that modifying the shape of a recharge pulse will produce paresthesia differences in the same manner that modifying the shape of a stimulation pulse will.

Figure 12:
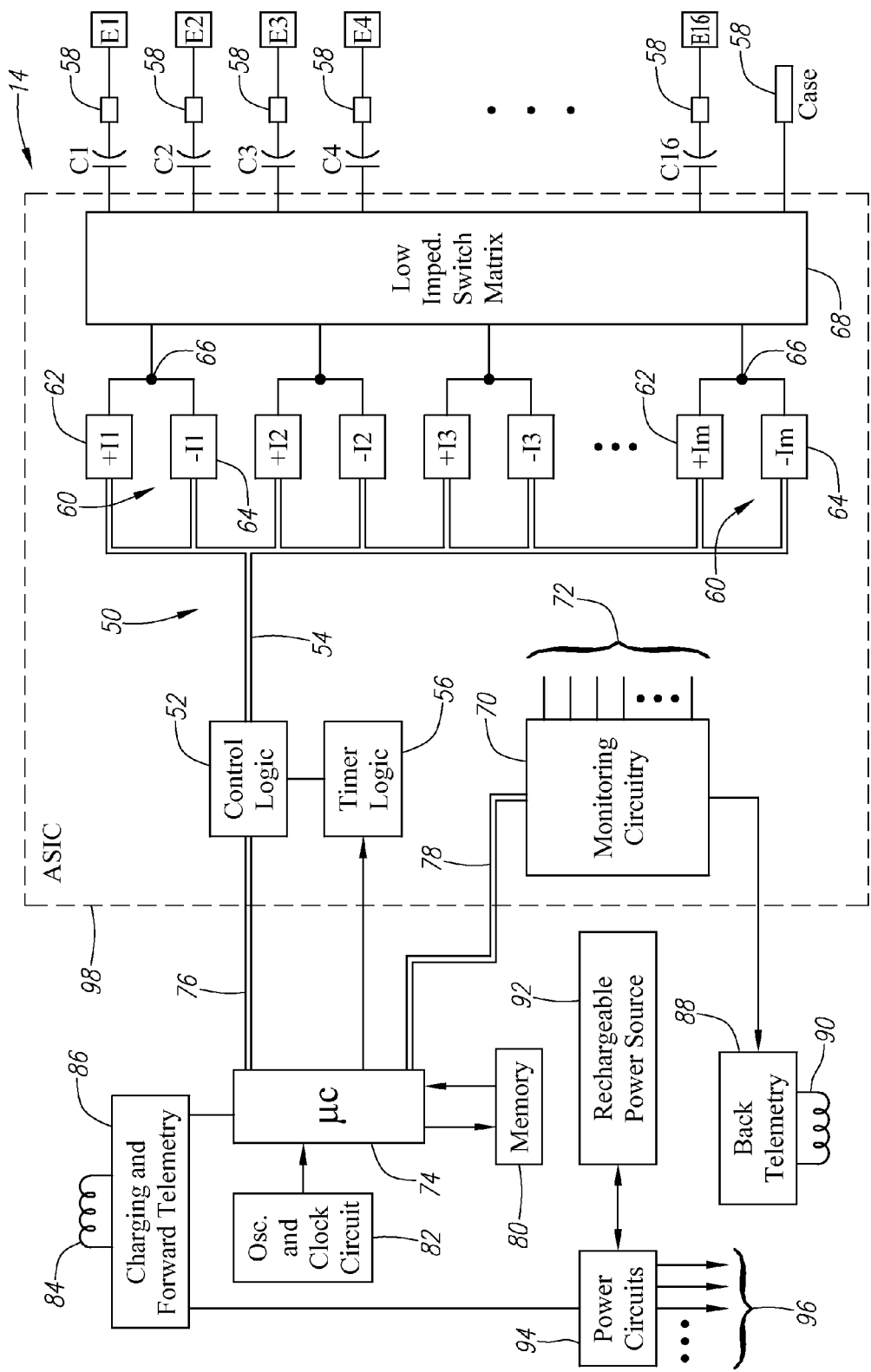
FIG. 12 is a block diagram of the internal components of the IPG of FIG. 2.

Turning next to FIG. 12, one exemplary embodiment of the IPG 14 will now be described. The IPG 14 includes stimulation output circuitry 50 configured for generating electrical stimulation energy in accordance with a defined pulsed waveform having a specified pulse amplitude, pulse rate, pulse width, and pulse shape under control of control logic 52 over data bus 54. Control of the pulse rate and pulse width of the electrical waveform is facilitated by timer logic circuitry 56, which may have a suitable resolution, e.g., 10 µs. The stimulation energy generated by the stimulation output circuitry 50 is output via capacitors C1-C16 to electrical terminals 58 corresponding to electrodes E1-E16.

In the illustrated embodiment, the stimulation output circuitry 50 comprises a plurality m independent current source pairs 60 capable of supplying stimulation energy to the electrical terminals 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66. The stimulation output circuitry 50 further comprises a low impedance switching matrix 68 through which the common node 66 of each current source pair 60 is connected to any of the electrical terminals 58 via the capacitors C1-C16.

Thus, for example, it is possible to program the first anodic current source 62 (+I1) to produce a pulse having a peak amplitude of +4 mA (at a specified rate and for a specified duration), and to synchronously program the second cathodic current source 64 (−I2) to similarly produce a pulse having a peak amplitude of −4 mA (at the same rate and pulse width), and then connect the node 86 of the anodic current source 62 (+I1) to the electrical terminal 58 corresponding to electrode E3, and connect the node 66 of the cathodic current source 64 (−I2) to the electrical terminal 58 corresponding to electrode E1.

Hence, it is seen that each of the programmable electrical terminals 58 can be programmed to have a positive (sourcing current), a negative (sinking current), or off (no current) polarity. Further, the amplitude of the current pulse being sourced or sunk from a given electrical terminal 58 may be programmed to one of several discrete levels. In one embodiment, the current through each electrical terminal 58 can be individually set from 0 to ±10 mA in steps of 100 µA, within the output voltage/current requirements of the IPG 14. Additionally, in one embodiment, the total current output by a group of electrical terminals 58 can be up to ±20 mA (distributed among the electrodes included in the group). Moreover, it is seen that each of the electrical terminals 58 can operate in a multipolar mode, e.g., where two or more electrical terminals are grouped to source/sink current at the same time. Alternatively, each of the electrical terminals 58 can operate in a monopolar mode where, e.g., the electrical terminals 58 are configured as cathodes (negative), and case of the IPG 14 is configured as an anode (positive).

It can be appreciated that an electrical terminal 58 may be assigned an amplitude and included with any of up to k possible groups, where k is an integer corresponding to the number of channels, and in one embodiment, is equal to 4, and with each channel k having a defined pulse amplitude, pulse width, pulse rate, and pulse shape. Other channels may be realized in a similar manner. Thus, each channel identifies which electrical terminals 58 (and thus electrodes) are selected to synchronously source or sink current, the pulse amplitude at each of these electrical terminals, and the pulse width, pulse rate, and pulse shape.

In an alternative embodiment, rather than using independent controlled current sources, independently controlled voltage sources for providing stimulation pulses of a specified and known voltage at the electrical terminals 58 can be provided. The operation of this output stimulation circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

Figure 13A:
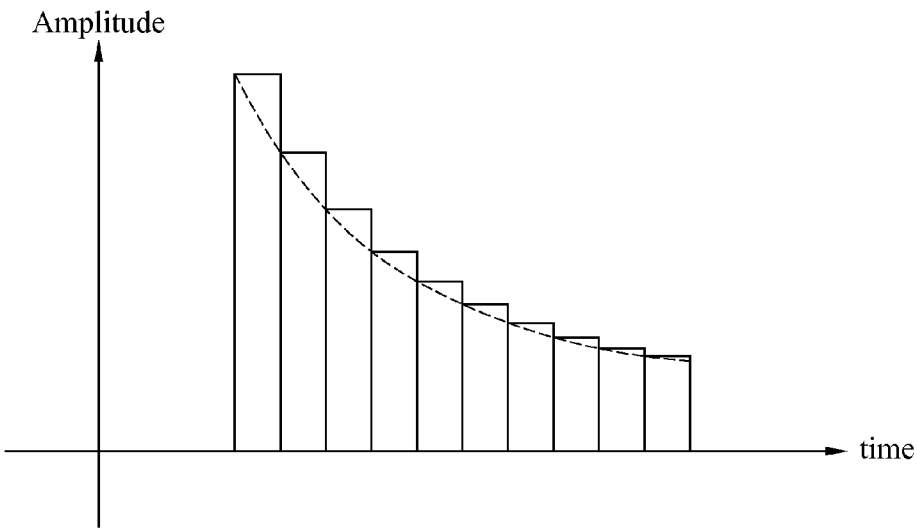
FIGS. 13A and 13B are diagrams of a negatively sloping exponential pulse and a positively sloping exponential pulse generating using step-wise amplitude levels.
Figure 13B:
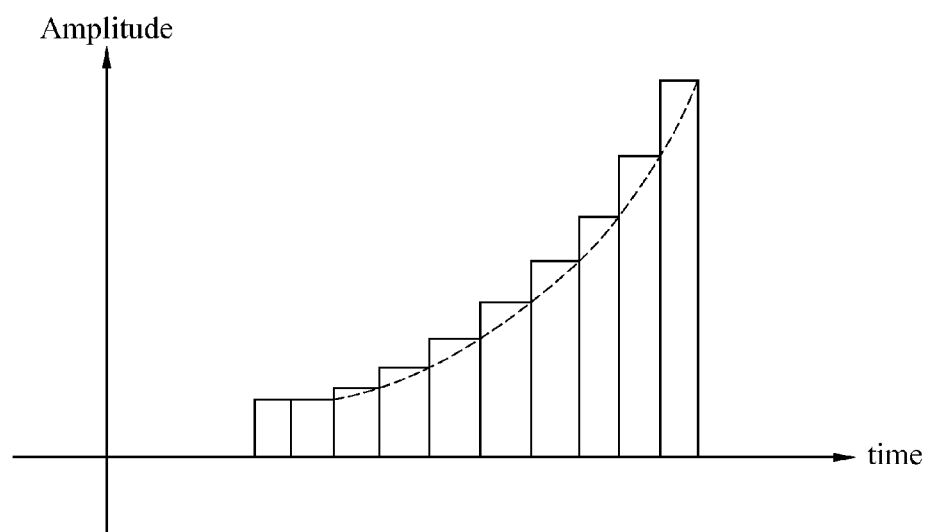
Figure 13C:
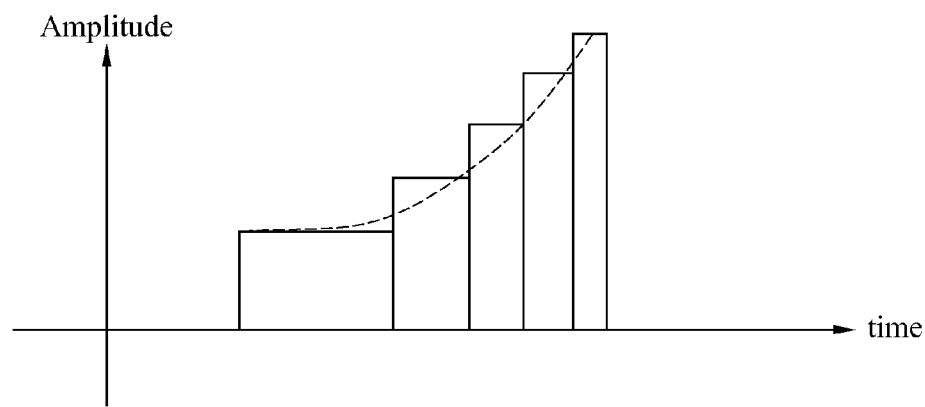
FIG. 13C is a diagram of a positively sloping exponential pulse generating using sub-pulses of varying duration.

It can be appreciated from the foregoing that the shape of each stimulation pulse output by the output stimulation circuitry 50 can be formed of a stepwise function of amplitude levels. For example, as shown in FIG. 13A, a negatively sloping exponential pulse can be formed by a series of gradually decreasing amplitude levels, and as shown in FIG. 13B, a positively sloping exponential pulse can be formed of a series of gradually increasing amplitude levels. Given a resolution of 10 µs and a pulse width of 100 µs, each of the pulsed waveforms illustrated in FIGS. 13A and 13B can be formed with ten discrete amplitude steps. Additionally, the overall pulse may be made up of sub-pulses of varying amplitude and sub-pulse duration as shown in FIG. 13C. This may allow good approximation of some waveforms by using fewer sub-pulses.

Figure 14:
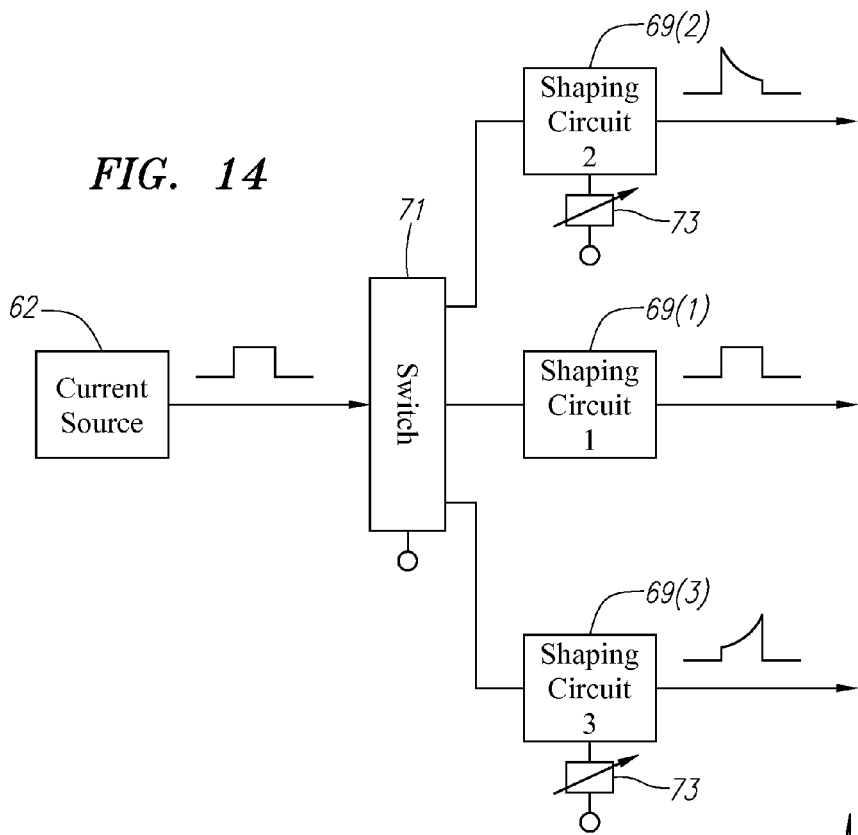
FIG. 14 is a block diagram of a portion of output stimulation circuitry used in the IPG of FIG. 12 used to generate different pulse shapes.

Alternatively, rather than forming the pulse waveform using a stepwise function of amplitude levels, the output stimulation circuitry 50 may include one or more analog circuits that are configured to shape the stimulation pulse output by each current source 62. For example, as shown in FIG. 14, the output stimulation circuitry 50 may comprise a plurality of different analog shaping circuits 69(1)-69(3) coupled to the output of each current source 62 via a switch 71 in order to shape a square pulse output from the respective current source 62 into a selected one of different pulse shape types. For example, the shaping circuit 69(1) may pass the square pulse through without modification, the shaping circuit 69(2) may transform the square pulse into a negatively sloping exponential pulse, and the shaping circuit 69(3) may transform the square pulse into a positively sloping exponential pulse. Each of the shaping circuits 69(2) and 69(3) may comprise at least one analog electrical component 73 having an electrical characteristic (e.g., capacitance or inductance) that can be adjusted to modify the pulse shape type; for example, by modifying the time constant of the pulse shape.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). Measuring electrode impedance is important, because implanted electrical stimulation systems depend upon the stability of the devices to be able to convey electrical stimulation pulses of known energy to the target tissue to be excited. The target tissue represents a known electrical load into which the electrical energy associated with the stimulation pulse is to be delivered. If the impedance is too high, that suggests the connector 42 and/or lead 12 (shown in FIG. 2), which connect with an electrode 26 may be open or broken. If the impedance is too low, that suggests that there may be a short circuit somewhere in the connector 42 and/or lead 12. In either event (too high or too low impedance), the IPG 14 may be unable to perform its intended function.

Measurement of the electrical parameter data also optionally facilitates control of the pulse shape output by the output circuitry 50, as will be described in further detail below. The electrical parameter data can be measured using any one of a variety means. For example, the electrical parameter data measurements can be made on a sampled basis during a portion of the time while the electrical stimulus pulse is being applied to the tissue, or immediately subsequent to stimulation, as described in U.S. patent application Ser. No. 10/364,436, entitled "Neural Stimulation System Providing Auto Adjustment of Stimulus Output as a Function of Sensed Impedance," which is expressly incorporated herein by reference. Alternatively, the electrical parameter data measurements can be made independently of the electrical stimulation pulses, such as described in U.S. Pat. Nos. 6,516,227 and 6,993,384, which are expressly incorporated herein by reference.

The IPG 14 further comprises processing circuitry in the form of a microcontroller (μC) 74 that controls the control logic 52 over data bus 76, and obtains status data from the monitoring circuitry 70 via data bus 78. The IPG 14 additionally controls the timer logic 56. The IPG 14 further comprises memory 80 and an oscillator and clock circuit 82 coupled to the microcontroller 74. Thus, the microcontroller 74, in combination with the memory 80 and oscillator and clock circuit 82, comprise a microprocessor system that carries out a program function in accordance with a suitable program stored in the memory 80. Alternatively, for some applications, the function provided by the microprocessor system may be carried out by a suitable state machine.

The microcontroller 74 generates the necessary control and status signals, which allow the microcontroller 74 to control the operation of the IPG 14 in accordance with the operating program and stimulation parameters stored in the memory 80. In controlling the operation of the IPG 14, the microcontroller 74 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, and to control and modify the polarity, pulse amplitude, pulse rate, pulse width, pulse shape, and channel through which the current stimulus pulses are provided.

In the case where the shape of the stimulation pulse is defined using a stepwise function of amplitude levels, the microcontroller 74 accordingly generates the amplitude steps (e.g., at either fixed 10 μs steps or steps with variable sub-pulse durations) at the electrodes 26 using the stimulation output circuit 50, in combination with the control logic 52 and timer logic 56, to shape the stimulation pulses. In the case where the shape of the stimulation pulses is defined using the analog shaping circuits 69, the microcontroller 74 uses the control logic 52 to accordingly select the shaping circuit 69 corresponding to the pulse shape type desired via the switch 71, and if the shaping circuit 69 comprises an analog an electrical circuit 73, adjusts its electrical characteristic.

In the illustrated embodiment, the microcontroller 74 modifies the pulse shape and the other pulse parameters (i.e., pulse amplitude, pulse width, and pulse rate) independent of each other. In a particularly advantageous embodiment, the microcontroller 74 modifies the pulse shape and the other pulse parameters dependent upon each other; that is, the microcontroller 74 may modify the other pulse parameter(s) in response to the modification of the pulse shape, or may modify the pulse shape in response to the modification of other pulse parameter(s). For example, the microcontroller 74 may modify the other pulse parameter(s) in response to the modification of the pulse shape to maintain a substantially uniform charge of the electrical stimulation energy. This can be accomplished by ensuring that the area under the pulse (e.g., by integrating the equation defining the pulse) remains constant (e.g., by changing the pulse amplitude or pulse width) as the pulse shape changes.

Figure 15:
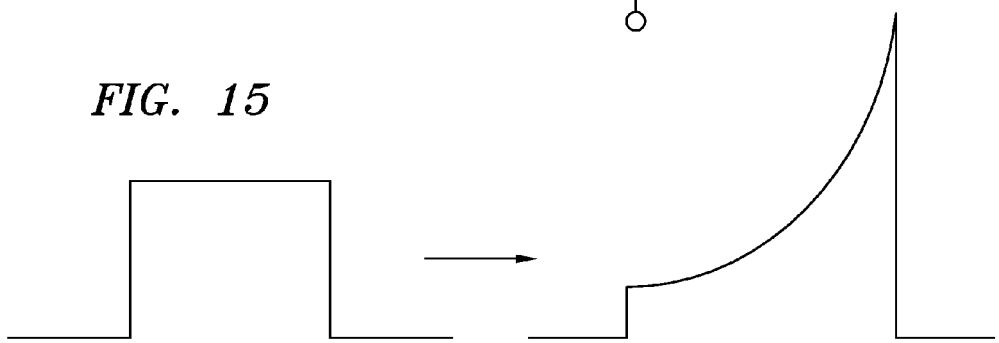
FIG. 15 is a diagram showing the changing of a square pulse to a positively sloping exponential pulse.

For example, if the pulse shape changes from a square pulse shape to a positively sloping exponential pulse shape, as illustrated in FIG. 15, the area under the pulse, and thus the charge of the stimulation energy, may be decreased without modifying any of the pulse parameters. However, if the amplitude and/or duration of the pulse is increased, the area under the pulse, and thus the charge of the stimulation energy, may be maintained. In the illustrated embodiment, it is the RC 16 that calculates the amplitude and/or duration of the pulse in response to the changing pulse shape, as will be described in further detail below, although such calculation can alternatively be performed by the microcontroller 74.

In an optional embodiment, the microcontroller 74 is configured for modifying the pulse shape based on electrical characteristics of the tissue measured by the monitoring circuitry 70. That is, because the electrical characteristics of the tissue through which the electrical stimulation energy is conveyed between the electrodes 26 may alter the characteristics of the stimulation pulses, and in particular the shape of the pulses, generated by the output stimulation circuitry 50 from its designed pulse shape (especially with output stimulation circuitry utilizing voltage sources), it may be desirable to match the actual pulse shape with the intended shape or otherwise change the pulse shape to achieve the desired clinical effect taking the electrical characteristics of the tissue into account.

Figure 16:
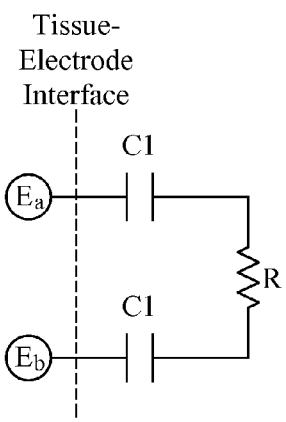
FIG. 16 is an exemplary equivalent circuit that can be created at an tissue electrode interface.

For example, the microcontroller 74 may create an equivalent resistance and capacitance circuit at the interface between electrodes $E_a$, $E_b$ and the tissue (i.e., the electrode-tissue interface), as illustrated in FIG. 16, based on a tissue impedance measured by the monitoring circuitry 70. With knowledge of the resistance value R and capacitance values C1, C2 in this equivalent circuit, the microcontroller 74 may then calculate the pulse shape that should be input into the equivalent circuit to output the desired pulse shape to otherwise achieve the desired clinical effect. In one embodiment, the microcontroller 74 automatically performs this pulse shape adjustment in response to changes in the electrical characteristics of the tissue, and in particular the tissue impedance, measured by the monitoring circuitry 70 (e.g., due to increasing fibrosis, patient motion, lead migration, etc.). In another embodiment, the microcontroller 74 only performs this pulse shape adjustment at certain time; for example, during programming of the IPG 14 with the stimulation parameters. In this case, the RC 16 may alternatively create the equivalent resistance and capacitance circuit based on the measured tissue impedance, and then calculate the pulse shape based on this equivalent circuit.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

As shown in FIG. 12, much of the circuitry included within the IPG 14 may be realized on a single application specific integrated circuit (ASIC) 98. This allows the overall size of the IPG 14 to be quite small, and readily housed within a suitable hermetically-sealed case. Alternatively, most of the circuitry included within the IPG 14 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 14, including providing power regulation, stimulus output, impedance measurement and monitoring. A digital IC (DigIC) may be provided to function as the primary interface between the processor IC and analog IC by controlling and changing the stimulus levels and sequences of the current output by the stimulation circuitry in the analog IC when prompted by the processor IC.

It should be noted that the diagram of FIG. 12 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, stimulation parameters can be programmed into or otherwise modified within the IPG 14 by the RC 16 and/or CP 18, thereby setting or otherwise changing the characteristics of the electrical stimulation energy generated and output by the IPG 14 to the electrodes 26. In the illustrated embodiment, this is accomplished by telemetrically transmitting instructions containing the stimulation parameters from the IPG 14 and/or CP 18 to the IPG 14. Alternatively, instructions without the stimulation parameters can be transmitted from the RC 16 and/or CP 18 to the IPG 14 to otherwise change the stimulation parameters stored in the IPG 14.

Figure 17:
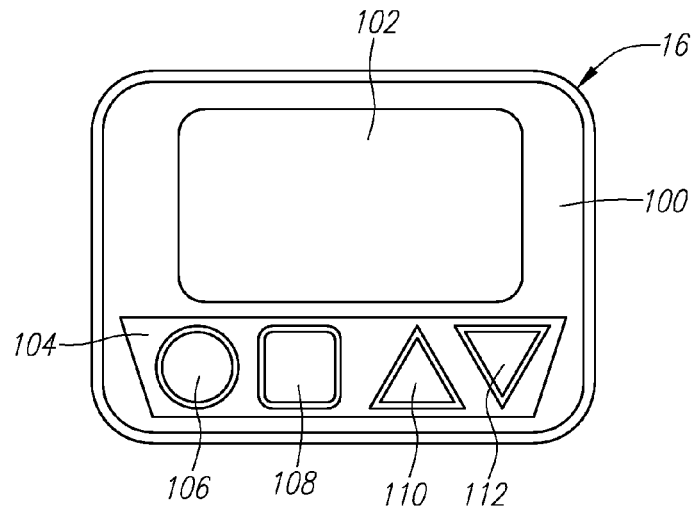
FIG. 17 is a plan view of a hand-held remote control (RC) that can be used in the neurostimulation system of FIG. 2.

Referring now to FIG. 17, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can actuated to increment or decrement any of stimulation parameters of the pulse generated by the IPG 14, including pulse amplitude, pulse width, pulse rate, and pulse shape. For example, the selection button 108 can be actuated to place the RC 16 in an "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, a "Pulse Rate Adjustment Mode," during which the pulse rate can be adjusted via the up/down buttons 110, 112, and a "Pulse Shape Adjustment Mode," during which the pulse shape can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters.

Figure 18:
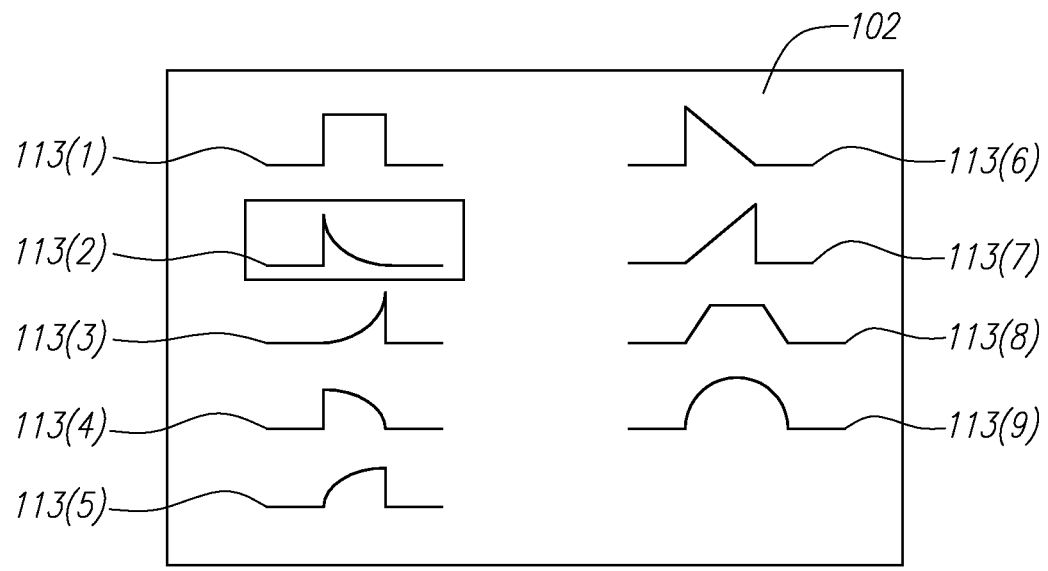
FIG. 18 is a plan view of a display screen generated by the RC of FIG. 17 to provide a means for the user to select a pulse shape type.
Figure 19:
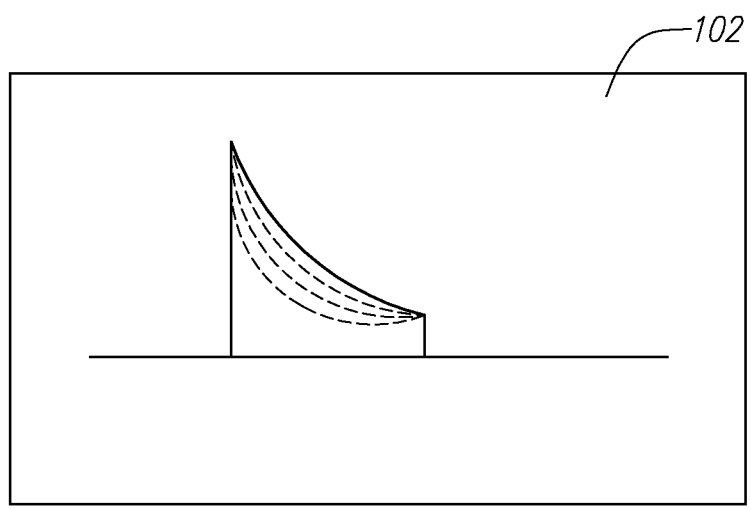
FIG. 19 is a plan view of a display screen generated by the RF of FIG. 17 that displays the current pulse shape generated by the IPG of FIG. 2.

Significant to the present inventions, placement of the RC 16 in the Pulse Shape Adjustment Mode allows the user to select the type of pulse shape and the slope characteristic, and in particular the time constant, of the selected pulse shape type. For example, FIG. 18 illustrates an exemplary display screen having identifiers in the form of icons, although text can be alternatively or optionally used. In particular, the display screen includes a square pulse icon 113(1), a negatively sloping exponential pulse icon 113(2), a positively sloping exponential pulse icon 113(3), a negatively sloping logarithmic pulse icon 113(4), a positively sloping logarithmic pulse icon 113(5), a negatively sloping ramped pulse icon 113(6), a positively sloping ramped pulse icon 113(7), a trapezoidal waveform icon 113(8), and a sinusoidal waveform icon 113(9) that a user may scroll through and highlight (negatively sloping exponential pulse icon 113(2) shown identified) by actuating the up/down buttons 110, 112. The button 108 can be actuated to then select the highlighted pulse shape type. Alternatively, rather than highlighting a pulse icon 113 by scrolling up/down using the up/down buttons 110, 112, a check box (not shown) associated with each pulse shape type can be checked by, e.g., touching it with a stylet or finger in the case where the display screen 102 has touchscreen capabilities. Alternatively, a single-button toggle may be used to switch between the different pulse shape types. Within each selected pulse shape type, the slope changing characteristics may be changed (e.g., by increasing or decreasing a time constant) by actuating the up/down buttons 110, 112. For example, FIG. 19 illustrates an exemplary display screen displaying the current pulse shape (in this case, the negatively sloping exponential pulse) as the up/down buttons 110, 112 are actuated to change the time slope of the pulse (previous pulse shapes shown in phantom). In an optional embodiment, a shape-cycle mode can automatically present different pulse shapes in a cycling fashion (changing every 3-5 seconds, for example), thereby allowing the user to experience many different pulse shapes quickly. When the user experiences an optimum stimulation, the user may actuate a button that selects the currently presented pulse shape. The pulse shape may be displayed to the user as it is presented, or alternatively, may be transparent to the user.

Figure 20:
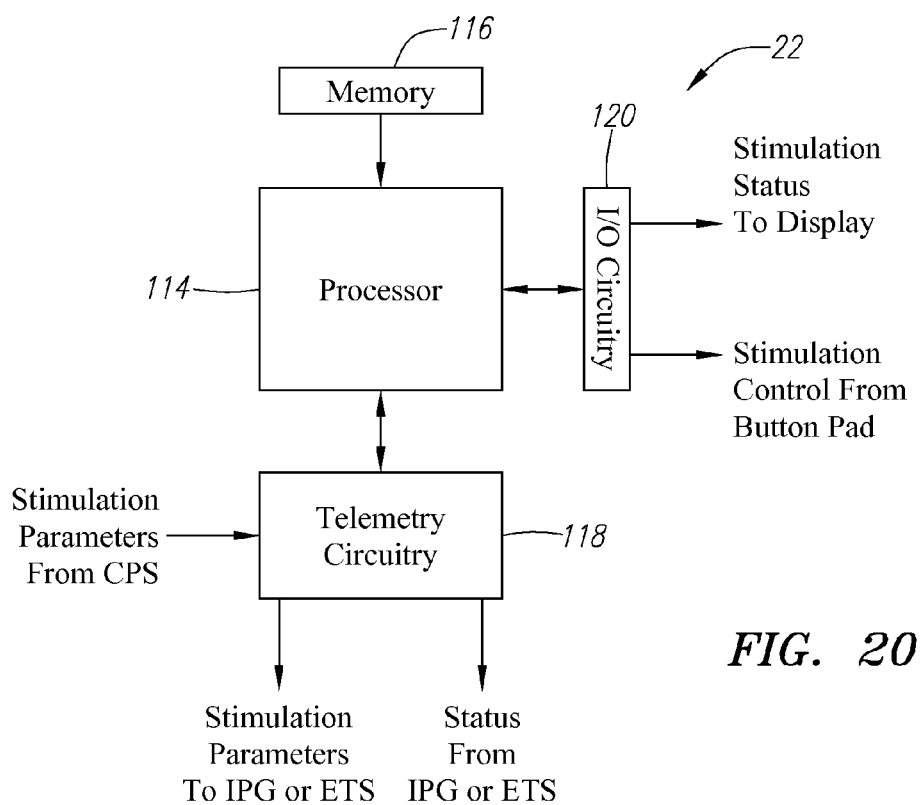
FIG. 20 is a block diagram of the internal components of the RC of FIG. 17.

Referring to FIG. 20, the internal components of an exemplary RC 16 will now be described. The RC 16 generally includes a processor 114 (e.g., a microcontroller), memory 116 that stores an operating program for execution by the processor 114, as well as stimulation parameters, input/output circuitry, and in particular, telemetry circuitry 118 for outputting stimulation parameters to the IPG 14 and receiving status information from the IPG 14, and input/output circuitry 120 for receiving stimulation control signals from the button pad 104 and transmitting status information to the display screen 102 (shown in FIG. 18). As well as controlling other functions of the RC 16, which will not be described herein for purposes of brevity, the processor 114 generates a plurality of stimulation parameter sets that define the pulse amplitude, pulse width, pulse rate, and pulse shape in response to the user operation of the button pad 104. These new stimulation parameter sets would then be transmitted to the IPG 14 via the telemetry circuitry 118, thereby adjusting the stimulation parameters stored in the IPG 14 and/or programming the IPG 14. The telemetry circuitry 118 can also be used to receive stimulation parameters from the CP 18. Further details of the functionality and internal componentry of the RC 16 are disclosed in U.S. Pat. No. 6,895,280, which has previously been incorporated herein by reference.

As described above with respect to the IPG 14, the pulse shape and the other pulse parameters, in the illustrated embodiment, are modified independent from each other. In this case, the processor 114 is configured for defining the pulse shape and the other pulse parameters in each stimulation parameter set independent of each other. However, if the pulse shape and the other pulse parameters are advantageously modified dependent upon each other, the processor 114 may be configured for defining the pulse shape and the other pulse parameters in each stimulation parameter set dependent upon each other; for example, by defining the other pulse parameters in response to the definition of a pulse shape to maintain the electrical charge between the stimulation parameter sets uniform.

As briefly discussed above, modifying and programming the stimulation parameters in the programmable memory of the IPG 14 after implantation can also be performed by a physician or clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord. As shown in FIG. 1, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and to subsequently program the IPG 14 (or ETS 20) with the optimum stimulation parameters. Thus, the functionality of the CP 18 is similar to that of the RC 18, with the exception that it greatly simplifies the programming of the optimum stimulation parameters. Further details discussing CPs and other programming devices are disclosed in U.S. Pat. Nos. 6,393,325 and 6,909,917, which are expressly incorporated herein by reference.

Figure 21:
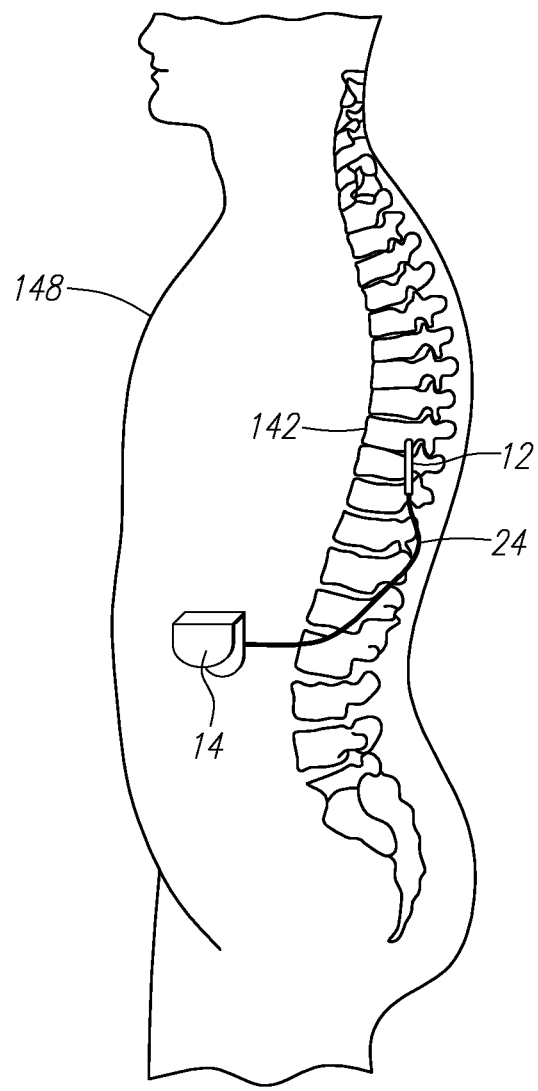
FIG. 21 is a plan view of the SCS system of FIG. 1 in use with a patient.

Having described the structure and function of the SCS system 10, a method of implanting and operating the system 10 will now be described. Referring to FIG. 21, the stimulation leads 12 are implanted within the spinal column 142 of a patient 140. The preferred placement of the stimulation leads 12 is adjacent, i.e., in the epidural space above the spinal cord area to be stimulated. The ETS 20 may then be coupled to the stimulation leads 12 via the percutaneous extension 28 and external cable 30 (not shown in FIG. 21), and then operated to deliver electrical stimulation energy to the electrodes 26 in accordance with a defined waveform. The pulse parameters of the waveform (including the pulse amplitude, pulse duration, pulse rate, and pulse shape) may be modified under control of the CP 18, thereby changing the characteristics of the electrical stimulation energy delivered from the electrodes 26 to the tissue, and allowing the efficacy of the stimulation provided to the patient 140 to be tested. The CP 18 can then be used to program the optimum stimulation parameters into the ETS 20.

After the trial period is over (typically 1-2 weeks), the IPG 14 is implanted within the patient 140 and coupled to the stimulation leads 12. Due to the lack of space near the location where the stimulation leads 12 exit the spinal column 140, the IPG 14 is generally implanted in a surgically-made pocket either in the abdomen or above the buttocks. The IPG 14 may, of course, also be implanted in other locations of the patient's body. The lead extension(s) 24 facilitate locating the IPG 14 away from the exit point of the stimulation leads 12. In the same manner briefly described above with respect to the ETS 20, the IPG 14 can then be operated and programmed with the optimum stimulation parameters under control of the CP 18. Under control of the patient, the RC 16 can subsequently be used to select stimulation programs or otherwise modify the stimulation parameters previously programmed into the IPG 14 to change the therapy.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable electrical tissue stimulation system, comprising:
   one or more electrical terminals configured for being coupled to one or more stimulation leads;
   output stimulation circuitry configured for outputting electrical stimulation energy to the one or more electrical terminals in accordance with a defined waveform; and
   control circuitry configured for receiving a user input specifying one of a negatively sloping pulse and a positively sloping pulse, the control circuitry further configured for modifying a pulse shape of the defined waveform by selecting the specified one of the negatively sloping pulse and the positively sloping pulse, thereby changing the characteristics of the electrical stimulation energy outputted to the one or more electrical terminals.

2. The electrical stimulation system of claim 1, wherein the negatively sloping pulse is a negatively sloping exponential pulse, and the positively sloping pulse is a positively sloping exponential pulse.

3. The electrical stimulation system of claim 1, wherein the negatively sloping pulse is a negatively sloping linear ramp pulse, and the positively sloping pulse is a positively sloping linear ramp pulse.

4. The electrical stimulation system of claim 1, wherein the control circuitry is configured for modifying a pulse shape of the defined waveform and at least one other pulse parameter dependent on each other in response to the user input.

5. The electrical stimulation system of claim 4, wherein the control circuitry is configured for modifying the at least one other pulse parameter in response to the modification of the pulse shape to maintain a substantially uniform charge of the electrical stimulation energy.

6. The electrical stimulation system of claim 1, further comprising monitoring circuitry configured for measuring one or more electrical characteristics of the tissue, wherein the control circuitry is configured for modifying the pulse shape based on the measured one or more electrical characteristics.

7. The electrical stimulation system of claim 6, wherein the control circuitry is configured for modifying the pulse shape in response to a change in the measured one or more electrical characteristics.

8. The electrical stimulation system of claim 1, wherein the output stimulation circuitry comprises a plurality of different analog shaping circuits, and the control circuitry is configured for modifying the pulse shape by selecting one of the different analog shaping circuits.

9. The electrical stimulation system of claim 1, wherein the control circuitry is configured for modifying the pulse shape by adjusting a characteristic of at least one analog electrical component in the output stimulation circuitry.

10. The electrical stimulation system of claim 1, wherein the defined waveform is formed of a stepwise function of amplitude levels or sub-pulse durations, and wherein the control circuitry is configured for modifying the pulse shape by adjusting the amplitude levels or sub-pulse durations.

11. The electrical stimulation system of claim 1, further comprising a stimulation lead carrying at least one electrode electrically coupled to the one or more electrical terminals.

12. The electrical stimulation system of claim 1, further comprising memory capable of storing a parameter defining the pulse shape.

13. The electrical stimulation system of claim 1, further comprising telemetry circuitry capable of wirelessly receiving instructions from an external programmer to modify the pulse shape.

14. The electrical stimulation system of claim 1, further comprising a case containing the one or more electrical terminals, output stimulation circuitry, and control circuitry to form a neurostimulator.

15. The electrical stimulation system of claim 14, wherein the neurostimulator is implantable.

16. The electrical stimulation system of claim 1, wherein at least a portion of the negatively sloping pulse has an absolute magnitude that decreases relative to time, and at least a portion of the positively sloping pulse has an absolute magnitude that increases relative to time.

17. The electrical stimulation system of claim 1, wherein the negatively sloping pulse and the positively sloping pulse have the same polarity.

18. A programmer for a neurostimulator, comprising:
a user interface capable of receiving an input from a user that specifies one of a negatively sloping pulse and a positively sloping pulse;
a processor configured for generating a plurality of stimulation parameter sets defining a plurality of different pulse shapes by selecting the specified one of the negatively sloping pulse and the positively sloping pulse; and
output circuitry configured for transmitting the plurality of stimulation parameter sets to the neurostimulator.

19. The programmer of claim 18, wherein the negatively sloping pulse is a negatively sloping exponential pulse, and the positively sloping pulse is a positively sloping exponential pulse.

20. The programmer of claim 18, wherein the negatively sloping pulse is a negatively sloping linear ramp pulse, and the positively sloping pulse is a positively sloping linear ramp pulse.

21. The programmer of claim 18, wherein the processor is configured for defining the plurality of different pulse shapes and other pulse parameters in each stimulation parameter set dependent on each other.

22. The programmer of claim 21, wherein the processor is configured for defining at least one of the other pulse parameters in response to the definition of the pulse shape to maintain a substantially uniform charge between the respective stimulation parameter sets.

23. The programmer of claim 18, wherein the processor is configured for defining the plurality of different pulse shapes based on one or more measured electrical characteristics of tissue.

24. The programmer of claim 23, wherein the processor is configured for defining the plurality of different pulse shapes in response to a change in the measured one or more electrical characteristics.

25. The programmer of claim 18, wherein the user interface comprises an actuator, and wherein the processor is configured for generating the plurality of stimulation parameter sets in response to actuation of the actuator.

26. The programmer of claim 25, wherein the processor is configured for defining the plurality of different pulse shapes in response to actuation of the actuator.

27. The programmer of claim 18, wherein the output circuitry is telemetry circuitry capable of wirelessly transmitting the plurality of stimulation parameter sets to the neurostimulator.

28. The programmer of claim 18, wherein at least a portion of the negatively sloping pulse has an absolute magnitude that decreases relative to time, and at least a portion of the positively sloping pulse has an absolute magnitude that increases relative to time.

29. The programmer of claim 18, wherein the negatively sloping pulse and the positively sloping pulse have the same polarity.

* * * * *